(12) United States Patent
Konoike et al.

(10) Patent No.: US 6,831,178 B2
(45) Date of Patent: Dec. 14, 2004

(54) PROCESS FOR PREPARATION OF SULFONAMIDE DERIVATIVES AND CRYSTALS THEREOF

(75) Inventors: Toshiro Konoike, Amagasaki (JP); Akira Okuyama, Amagasaki (JP); Yoshiyuki Masui, Amagasaki (JP); Teruo Sakata, Amagasaki (JP)

(73) Assignee: Shionogi & Co., Ltd., Osaka (JP)

( * ) Notice: Subject to any disclaimer, the term of this patent is extended or adjusted under 35 U.S.C. 154(b) by 42 days.

(21) Appl. No.: 10/257,752

(22) PCT Filed: Apr. 16, 2001

(86) PCT No.: PCT/JP01/03216
§ 371 (c)(1),
(2), (4) Date: Oct. 17, 2002

(87) PCT Pub. No.: WO01/79201
PCT Pub. Date: Oct. 25, 2001

(65) Prior Publication Data
US 2003/0187050 A1 Oct. 2, 2003

(30) Foreign Application Priority Data
Apr. 19, 2000 (JP) .................................. 2000-117562

(51) Int. Cl.⁷ .......................................... C07D 209/02
(52) U.S. Cl. ................................................ 548/467
(58) Field of Search ........................................ 548/467

(56) References Cited

U.S. PATENT DOCUMENTS

| | | | |
|---|---|---|---|
| 5,459,248 A | 10/1995 | Silverberg et al. | |
| 5,629,456 A | 5/1997 | Yamada et al. | |
| 5,702,716 A | 12/1997 | Dunn et al. | |
| 6,207,698 B1 | 3/2001 | Wantanabe et al. | |
| 6,235,768 B1 * | 5/2001 | Wantanabe et al. | 514/414 |
| 6,727,266 B2 * | 4/2004 | Watanabe | 514/364 |

FOREIGN PATENT DOCUMENTS

| | | |
|---|---|---|
| EP | 0 312 208 | 4/1989 |
| EP | 0 522 569 | 1/1993 |
| EP | 0652226 | 5/1995 |
| JP | 11-246527 | 9/1999 |
| WO | 91/01720 | 2/1991 |
| WO | 9727174 | 7/1997 |
| WO | 97/32591 | 9/1997 |
| WO | 98/14222 | 4/1998 |
| WO | 98/40113 | 9/1998 |

OTHER PUBLICATIONS

Claudiu T. Supuran et al., "Protease inhibitors Part 7 Inhibition of Clostridium histolyticum collagenase with sulfonylated derivatives of L-valine hydroxamate", European Journal of Pharmaceutical Sciences, vol. 10, pp. 67–76, XP002235652, Mar. 2000.

I. A. Frankov et al., "Synthesis and Pharmacoloical Properties of 3-Carboxyalkylrhodanines Containing Alkylating Moieties", Database Crossfire Beilstein, Beilstein Institut zur Förderung der Chemischen Wissenschaften, Frankfurt am Main, DE; Pharm. Chem. J. 19 (8) 544–547, 1985, Database accession No. 3171675, XP002242970.

Sonogashira et al., "A Convenient Synthesis of Acetylenes: Catalytic Substitutions of Acetylenic Hydrogen With Bromoalkenes, Iodoarenes, and Bromopyridines", Tetrahedron Letters No. 50, pp. 4467–4470, 1975.

Thorand et al., "Improved Procedures for the Palladium–Catalyzed Coupling of Terminal Alkynes with Aryl Bromides (Sonogashira Coupling)", J. Org. Chem., vol. 63, 8551–8553, 1998.

Bumagin et al., "Catalytic Coupling of Terminal Acetylenes with Iodoarenes and Diaryliodonium Salts in Water", Tetrahedron Letters, Vol. 37, pp. 897–900, 1996.

Nguefack et al., "An Efficient Palladium–Catalysed Coupling of Terminal Alkynes with Aryl Halides under Jeffery's Conditions", Tetrahedron Letters, vol. 37, pp. 5527–5530, 1996.

* cited by examiner

*Primary Examiner*—Deborah C. Lambkin
(74) *Attorney, Agent, or Firm*—Wenderoth, Lind, & Ponack, L.L.P.

(57) ABSTRACT

A process for the preparation of a compound of the formula (I'):

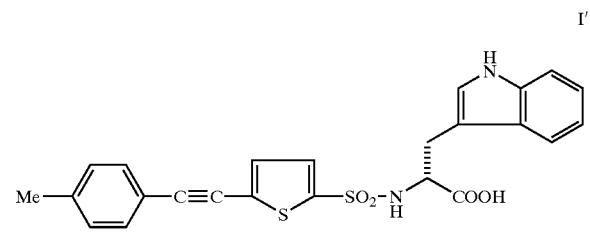

which comprises reacting in a solvent a compound of the formula (III):

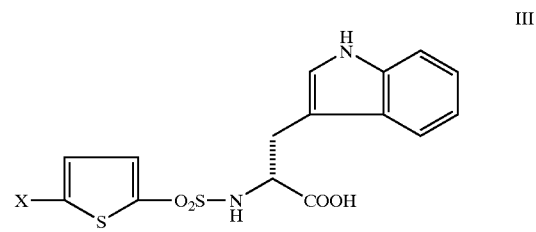

wherein X is halogen,
with p-tolylacetylene, a copper (I) salt, a catalyst, and a base, and then treating the resulting reaction mixture with an acid.

17 Claims, 3 Drawing Sheets

PROCESS FOR PREPARATION OF SULFONAMIDE DERIVATIVES AND CRYSTALS THEREOF

TECHNICAL FIELD

The present invention relates to a process for preparation of $N^\alpha$-[[2-[5-[[4-methylphenyl]ethynyl]thienyl]]sulfonyl]-D-tryptophan and crystals thereof.

BACKGROUND ART $N^\alpha$-[[2-[5-[[4-methylphenyl]ethynyl]thienyl]]sulfonyl]-D-tryptophan is disclosed in such as WO97/27174.

A coupling reaction (Sonogashira reaction) of a halogenated aryl and an acetylene derivative which is used as a key-step for the preparation of this compound, it is disclosed in WO97/27174 and Tetrahedron Lett. 1975, 4467–4470.

Generally, in Sonogashira reaction, a halogenated aryl, a halogenated heteroaryl etc. are reacted with an acetylene derivative in a solvent such as N,N-dimethylformamide in the presence of a copper iodide, a base and a palladium catalyst. An example of using ethyl acetate as a solvent and an example of using palladium on carbon as a catalyst have not been reported.

An example of Sonogashira reaction by using tetrahydrofuran as a solvent is disclosed in J. Org. Chem. 1998, 8551–8553.

An example of Sonogashira reaction by using a solvent containig water is disclosed in Tetrahedron Lett. 1996, 897–900 and Tetrahedron Lett. 1996, 5527–5530, but an example by using ethyl acetate and water as a solvent is not described.

Generally, in an industrial preparation, it is not preferred to use a solvent, such as N,N-dimethylformamide having a high mutual solubility for water, in view of a post-treatment of the reaction. Preferred is a solvent, such as acetic acid ester exampled as ethyl acetate, isopropyl acetate, isobutyl acetate, and-n-butyl acetate, or toluene, dichloromethane and the like, which have a low mutual solubility for water.

An organopalladium catalyst having such as a phosphine ligand, usually used in Sonogashira reaction, is high fat-soluble. Thus, in a case the resulting product is also high fat-soluble, it is difficult to separate the product and the organopalladium catalyst. Specially in a case for the preparation of medicaments, an amount of residual palladium may cause a serious problem because the upper limit of concentration of a heavy metal in a final bulk is regulated by the Japanese Pharmacopoeia.

$N^\alpha$-[[2-[5-[[4-methylphenyl]ethynyl]thienyl]]sulfonyl]-D-tryptophan is disclosed in such as WO97/27174, however a crystal form thereof is not disclosed.

DISCLOSURE OF INVENTION

An object of the present invention is to provide an industrial process for the preparation of $N^\alpha$-[[2-[5-[[4-methylphenyl]ethynyl]thienyl]]sulfonyl]-D-tryptophan suitable for the standard. Another object of the present invention is to prepare a crystal of $N^\alpha$-[[2-[5-[[4-methylphenyl]ethynyl]thienyl]]sulfonyl]-D-tryptophan which has a high stability and bioavailability.

In the above situation, the inventors of the present invention have studied and found a process for the preparation of $N^\alpha$-[[2-[5-[[4-methylphenyl]ethynyl]thienyl]]-sulfonyl]-D-tryptophan which is used as a medicament, and a crystal thereof.

The present invention relates to:

1) A process for the preparation of a compound of the formula (I'):

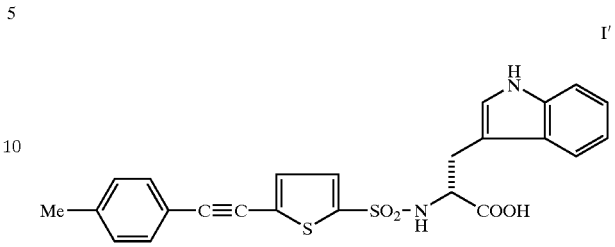

which comprises reacting in a solvent a compound of the formula (III):

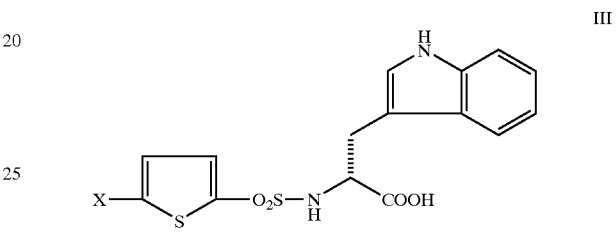

wherein X is halogen, with p-tolylacetylene, a copper (I) salt, a catalyst, and a base, and then treating the resulting reaction mixture with an acid.

In more detail, the invention relates to the following 2) to 21).

2) A process for the preparation of a compound of the formula (II):

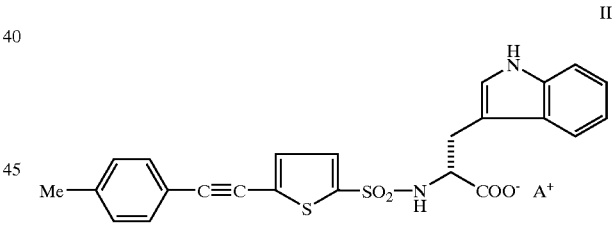

wherein $A^+$ is a cation derived from a basic substance, which comprises reacting in a solvent a compound of the formula (I'):

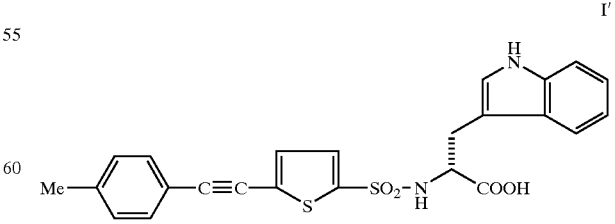

with the basic substance in the presence of an alcohol.

3) The process according to 2) wherein a starting material is the compound (I') obtained by the process according to 1).

4) A process for the preparation of a compound of the formula (I):

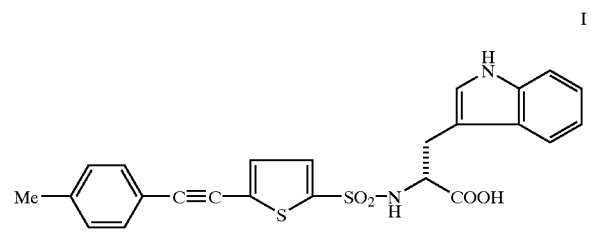

which comprises reacting a compound of the formula (II) obtained by the process according to 3):

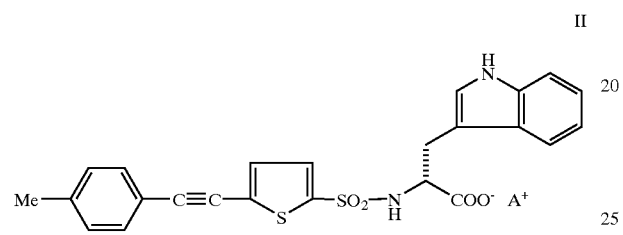

wherein $A^+$ is a cation derived from a basic substance, with an acid.

5) A process for the preparation of a compound of the formula (III):

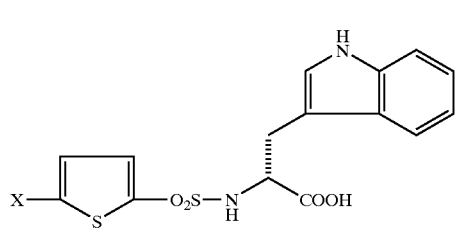

wherein X is halogen,
which comprises reacting in a solvent a compound of the formula (IV):

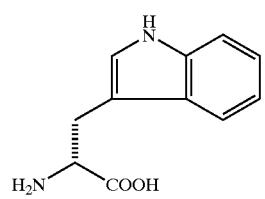

with a compound of the formula (V):

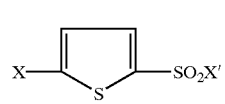

wherein X and X' are independently halogen,
in the presence of a base.

6) A process for the preparation of a compound of the formula (1):

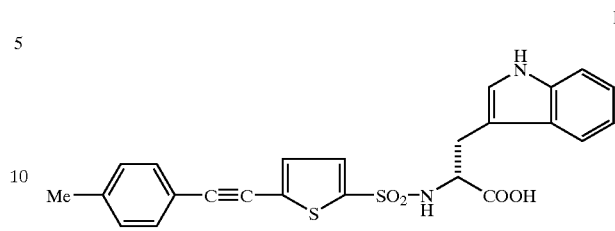

which comprises steps (1) to (4),
(1) a step for the preparation of a compound of the formula (III):

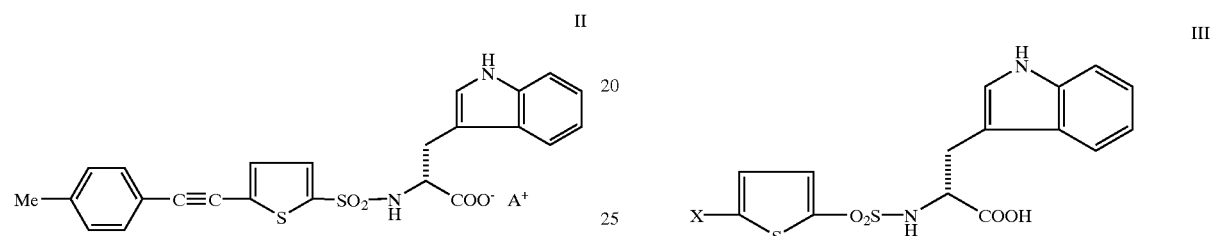

wherein X is halogen,
which comprises reacting in a solvent a compound of the formula (IV):

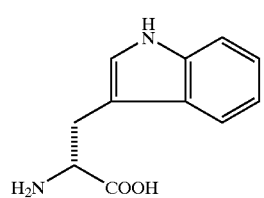

with a compound of the formula (V):

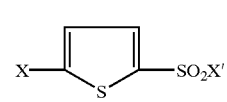

wherein X and X' are independently halogen,
in the presence of a base,
(2) a step for the preparation of a compound of the formula (I'):

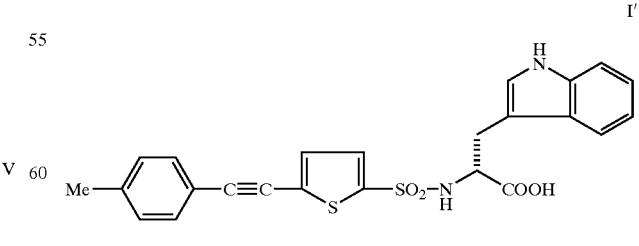

which comprises reacting in a solvent a compound of the formula (III) with p-tolylacetylene, a copper (I) salt, a catalyst, and a base, and then treating the resulting reaction mixture with an acid, (3) a step for the preparation of a compound of the formula (II):

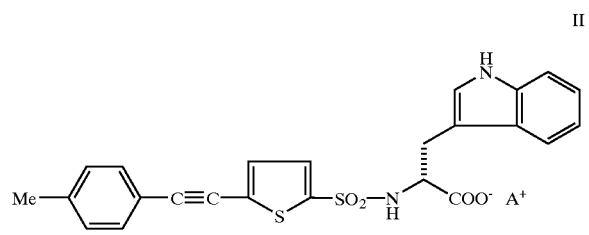

wherein A$^+$ is a cation derived from a basic substance, which comprises reacting in a solvent a compound of the formula (I'):

with a basic substance, (4) a step for the treatment of the compound (II) with an acid.

7) The process according to 1) wherein the solvent is N,N-dimethylformamide.
8) The process according to 1) wherein the solvent is a mixture of ethyl acetate and water.
9) The process according to 1) wherein the catalyst is selected from the group consisting of palladium black, palladium on carbon, bistriphenylphosphinepalladium (II) cholride, tetraxis(triphenylphosphine)palladium (0), palladium (II) oxide, palladium (II) chloride, palladium (II) bromide, and palladium (II) acetate.
10) The process according to 1) wherein the solvent is N,N-dimethylformamide, and the catalyst is palladium on carbon.
11) The process according to 1) wherein the solvent is a mixture of ethyl acetate and water, and the catalyst is bistriphenylphospinepalladium (II) chloride.
12) The process according to 1) wherein the solvent is a mixture of ethyl acetate and water, and the catalyst is tetraxis(triphenylphospine)palladium (0).
13) The process according to 2) wherein the alcohol is methanol.
14) The process according to 2) wherein the basic substance is sodium hydroxide or sodium methoxide.
15) The process according to 2) wherein the alcohol is methanol, and the basic substance is sodium hydroxide or sodium methoxide.
16) The process according to 5) wherein the solvent is a mixture of acetone and water, and the base is sodium carbonate.
17) A process for the preparation of a compound of the formula (I):

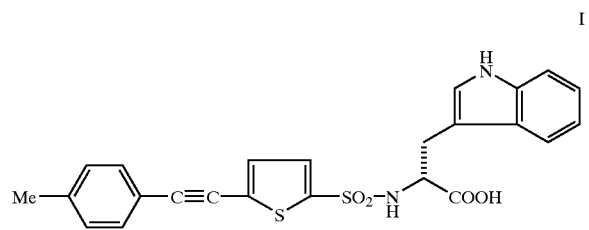

which comprises steps (1) to (2),
(1) a step for the preparation of a compound of the formula (II'):

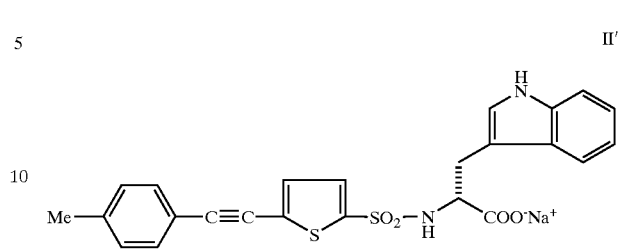

which comprises reacting in a mixture of ethyl acetate and water a compound of the formula (III):

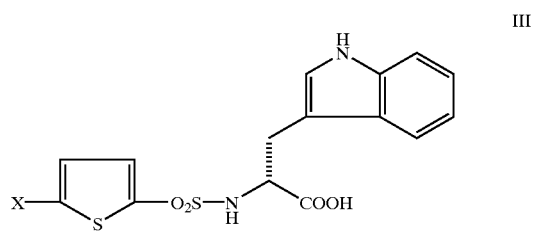

wherein X is halogen,
with p-tolylacetylene, a copper iodide or copper bromide, a bistriphenylphosphinepalladium (II) cholride or tetraxis (triphenylphosphine)palladium (0), and a base, and then treating the resulting reaction mixture with an acid, and then treating the resulting reaction mixture with sodium hydroxide or sodium methoxide in the presence of methanol.
(2) a step for the treatment of the compound (II') with an acid.
18) A compound of the formula (II''):

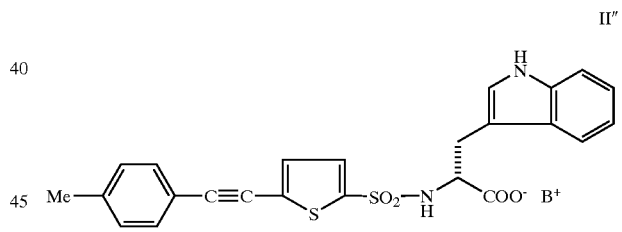

wherein B$^+$ is Na$^+$, K$^+$ or NH$_4^+$.
19) A crystal of N$^\alpha$-[[2-[5-[[4-methylphenyl]ethynyl] thienyl]]sulfonyl]-D-tryptophan wherein a powder X-ray diffraction pattern has a primary peak at a diffraction angle (2θ)=10.86, 18.14, 19.62, 21.60, 22.74, 23.38, 25.54, 27.22 and 28.12 (degree).
20) A crystal of N$^\alpha$-[[2-[5-[[4-methylphenyl]ethynyl] thienyl]]sulfonyl]-D-tryptophan wherein a powder X-ray diffraction pattern has a primary peak at a diffraction angle (2θ)=7.28, 11.18, 15.20, 16.58, 18.24, 21.20, 22.46, 25.66 and 33.16 (degree).
21) A crystal of N$^\alpha$-[[2-[5-[[4-methylphenyl]ethynyl] thienyl]]sulfonyl]-D-tryptophan wherein a powder X-ray diffraction pattern has a primary peak at a diffraction angle (2θ)=6.62, 10.46, 16.58, 16.82, 23.28 and 23.98 (degree).

In the present specification, examples of "cation derived from a basic substance" include a divalent cation such as Mg$^{2+}$, Ca$^{2+}$, Sr$^{2+}$, and Ba$^{2+}$ and a univalent cation such as Na$^+$, K$^+$, NH4$^+$, Li$^+$, Rb$^+$, and Cs$^+$. A univalent cation is preferabl is more preferable.

In the present specification, the term "halogen" means fluoro, chloro, bromo, and iodo.

BEST MODE FOR CARRYING OUT THE INVENTION

Figure 1:
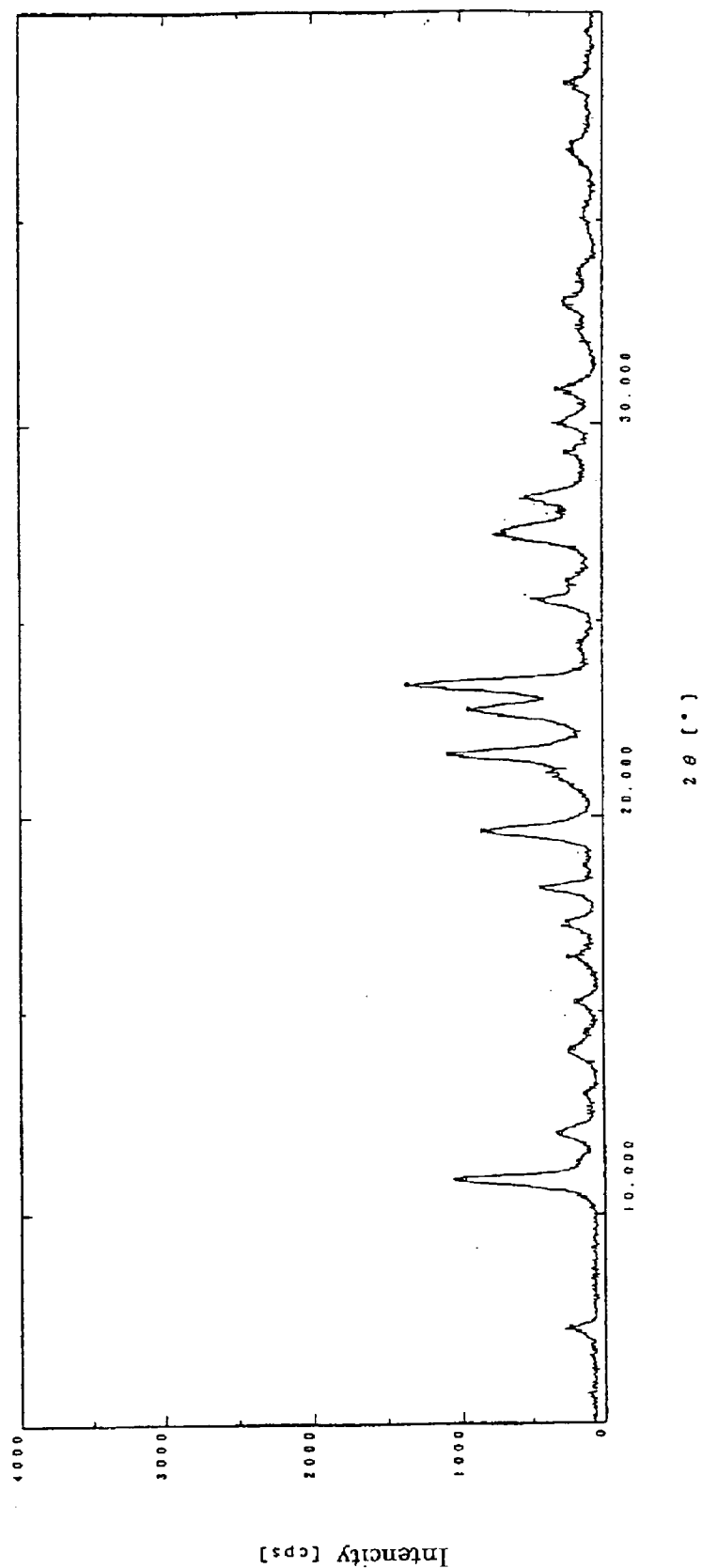
FIG. 1: The chart shows a powder X-ray diffraction of type A crystal obtained in Example 9.

The process for an industrial preparation of $N^{\alpha}$-[[2-[5-[[4-methylphenyl]-ethynyl]thienyl]]sulfonyl]-D-tryptophan from D-tryptophan (IV) as a starting material is shown in the following schema.

wherein X and X' are independently halogen; A is cation such as $Na^+$, $K^+$ and $NH_4^+$.

Each step is explained in detail below.

(Step 1)

This step is a coupling process of a starting material (IV) and a halogenosulufonylated compound (V) by using a Shotten-Baumann method. In a solvent, such as a mixture of water and acetone, a mixture of water and 1,4-dioxane, a mixture of water and tetrahydrofuran, a mixture of water and dimethoxyethane, a mixture of water and acetonitrile, N,N-dimethylformamide, N,N-dimethylacetamide, and dimethylsulfoxide, a compound (III) is obtained by reacting a compound (IV) with a compound (V) of 0.9 to 2 mol eq., preferably 1.0 to 1.2 mol eq. in the presence of a base of 2 to 10 mol eq., preferably 2 to 3 mol eq. at −20 to 30° C., preferably −5 to 10° C. for 1 to 20 h, more preferably 1 to 3 h, followed by usual post-treatment.

A mixture of acetone and water is preferable as a solvent. Preferably the ratio of acetone/water is 5/1 to 1/5, more preferably 2/1 to 1/2.

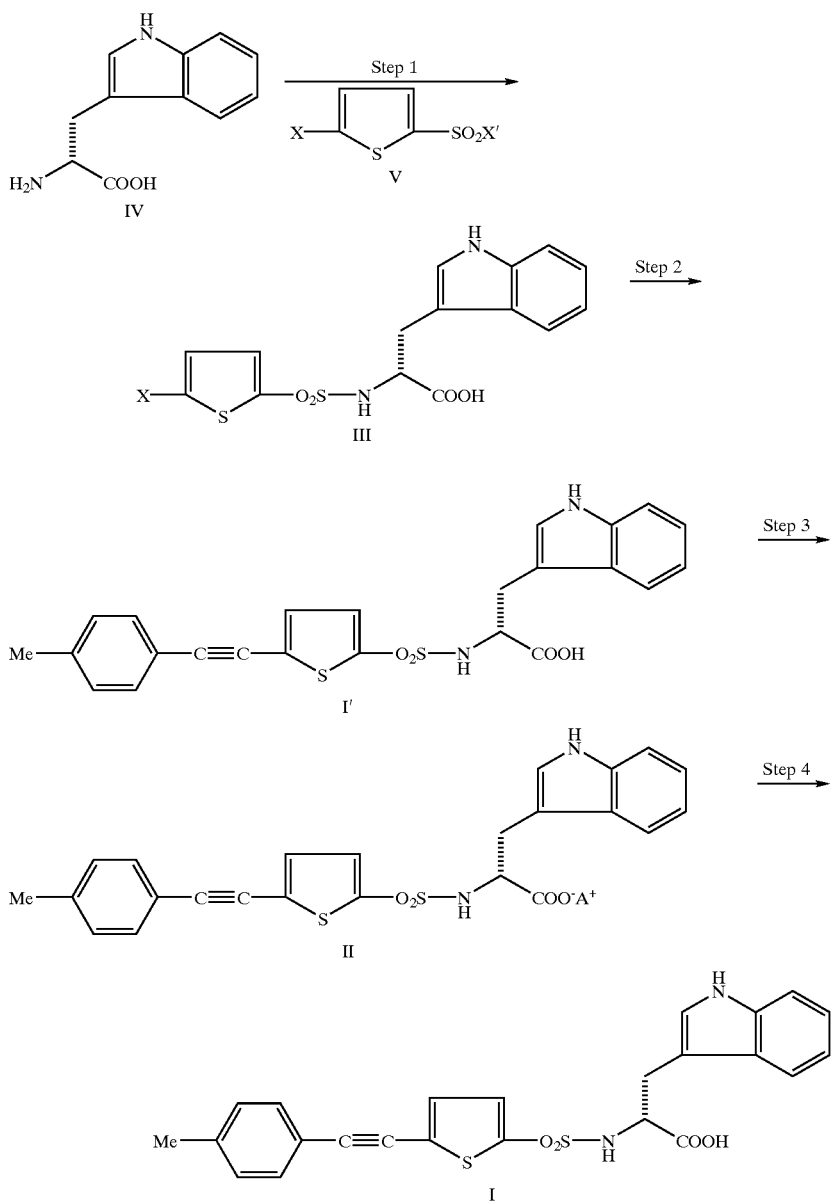

Examples of a base include an inorganic base such as sodium carbonate, sodium hydrogen carbonate, potassium carbonate, potassium hydrogen carbonate, cesium carbonate, cesium hydrogen carbonate, lithium carbonate, lithium hydrogen carbonate, rubidium carbonate, rubidium hydrogen carbonate, lithium hydroxide, sodium hydroxide, potassium hydroxide, rubidium hydroxide, cesium hydroxide, and ammonium carbonate, and a tertiary amine such as triethylamine, tributylamine, diisopropylethylamine. Sodium carbonate, potassium carbonate, cesium carbonate, sodium hydroxide, triethylamine, and the like are preferable as a base.

(Step 2)

This step is the coupling process of a compound (III) and p-tolylacetylene by using Sonogashira reaction. In the solvent, such as a mixture of acetic acid ester and water such as a mixture of ethyl acetate and water, a mixture of isopropyl acetate and water, a mixture of isobutyl acetate and water, a mixture of n-butyl acetate and water, or a mixture of tetrahydrofuran and water, a mixture of 1,4-dioxane and water, a mixture of dimethoxyethane and water, a mixture of toluene and water, N,N-dimethylformamide, N,N-dimethylacetamide, dimethylsulfoxide, tetrahydrofuran, dimethoxyethane and the like, a compound (I') is obtained by reacting a compound (III) with p-tolylacetylene using 0.8 to 5 mol eq., preferably 1 to 1.5 mol eq. in the presence of a copper (1) salt using 0.001 to 0.5 mol eq., preferably 0.005 to 0.05 mol eq., a base using 1 to 10 mol eq., preferably 2 to 4 mol eq., and a catalyst using 0.001 to 0.5 mol eq., preferably 0.002 to 0.05 mol eq. at 30 to 200° C., preferably 50 to 80° C. for 1 to 30 h, preferably 1.5 to 5 h, followed by an usual post-treatment. Besides the reaction mixture is used in Step 3-A as described below without post-treatment.

A mixture of ethyl acetate and water is preferable as a solvent. Preferably the ratio of ethyl acetate/water is 500/1 to 1/1, more preferably 100/1 to 100/10.

Examples of a copper (a) salt include copper (I) fluoride, copper (I) chloride, copper (I) bromide, copper (I) iodide, copper (I) oxide, copper (a) sulfide, copper (I) selenide, copper (I) acetate, copper (I) cyanide, copper.(I) thiocyanate, and copper (I) trifluoromethanesulfonate. Copper (I) chloride, copper (I) bromide, and copper (a) iodide are preferable as a copper (I) salt.

Examples of a base include a tertiary amine such as triethylamine, tributylamine, trimethylamine, diisopropylmethylamine, diisopropylethylamine, dimethylaniline, and methyldibenzylamine. Triethylamine, tributylamine, diisopropylethylamine and the like are preferable as a base.

Examples of a catalyst include palladium black, palladium on carbon, palladium (II) chloride, bisbenzonitrilepalladium (II) chloride, palladium (II) bromide, palladium (II) iodide, palladium (II) oxide, palladium (II) sulfide, palladium (II) acetate, palladium (II) propionate, palladium (II) sulfate, palladium (II) hydroxide, palladium (II) cyanide, palladium (II) trifluoroacetate, tetraxis(triphenylphospine) palladium (0), bistriphenylphospinepalladium (II) chloride, and tetraxis(triphenylphospine)palladium (0). Tetraxis(triphenylphospine)palladium (0) and bistriphenylphospine-palladium (II) chloride are preferable as a catalyst.

In the case of palladium on carbon used as a palladium catalyst, specially N,N-dimethylformamide, N,N-dimethylacetamide, N-methylpyrrolidone, and N,N-hexamethylphosphoramide are preferable as a solvent.

It is found that a reaction in this step can be proceeded in ethyl acetate which is useful for the industrial production.

Another discovery is that the reaction can be accelerated by adding water in the reaction system.

(Step 3)

Step 3 is a process for the preparation of a compound (II) by using the method described in Step 3-A or Step 3-B as follows.

A compound (II) is hardly soluble in water and an organic solvent. Therefore, after the treatment with an acid in Step 2, it is easy to remove an impurity such as an acetylene compound and a palladium catalyst included in the organic layer, and a copper salt and a base included in the aqueous layer.

(Step 3-A)

At post-treatment of Step 2, to the reaction mixture are added acetic acid ester such as ethyl acetate, isopropyl acetate, isobutyl acetate, n-butyl acetate, or dichloromethane, methyl isobutyl ketone, and the like as an extracting solvent, and an acid such as hydrochloric acid, sulfuric acid, methanesulfonic acid, phosphoric acid, nitric acid to acidify, and brine if necessary, and then the extract of a compound (II) is obtained. The extract is filtered through activated carbon if necessary, and converted to be basic by addition of an alcohol and a basic substance. To the extract is added a seed crystal if necessary, then the resulting crystal of a compound (III) is obtained.

Ethyl acetate is preferable as an extracting solvent.

Hydrochloric acid is preferable as an acid.

Examples of an alcohol include methanol, ethanol, n-propanol, isopropanol, n-butanol, and the like. Methanol is preferable.

Examples of a basic substance include sodium hydroxide, sodium methoxide, potassium hydroxide, ammonia, lithium hydroxide, cesium hydroxide, rubidium hydroxide, lithium methoxide, potassium methoxide, cesium methoxide, sodium ethoxide, lithium ethoxide, potassium ethoxide, cesium ethoxide, lithium carbonate, lithium hydrogen carbonate, sodium carbonate, sodium hydrogen carbonate, potassium carbonate, potassium hydrogen carbonate, rubidium carbonate, rubidium hydrogen carbonate, cesium carbonate, cesium hydrogen carbonate, and the like. Sodium hydroxide and sodium methoxide are preferable as a base.

(Step 3-B)

A compound (I') is dissolved in an acetic acid ester such as ethyl acetate, isopropyl acetate, isobutyl acetate, and n-butyl acetate, then the solution is filtered through activated carbon if necessary, and converted to be basic by addition of methanol and a basic substance. To the extract is added a seed crystal if necessary, then the resulting crystal of a compound (II) is obtained.

Ethyl acetate is preferable as an extracting solvent.

Examples of a basic substance include sodium hydroxide, sodium methoxide, potassium hydroxide, ammonia, lithium hydroxide, cesium hydroxide, rubidium hydroxide, lithium methoxide, potassium methoxide, cesium methoxide, sodium ethoxide, lithium, ethoxide, potassium ethoxide, cesium ethoxide, lithium carbonate, lithium hydrogen carbonate, sodium carbonate, sodium hydrogen carbonate, potassium carbonate, potassium hydrogen carbonate, rubidium carbonate, rubidium hydrogen carbonate, cesium carbonate, cesium hydrogen carbonate, and the like. Sodium hydroxide and sodium methoxide are preferable as a base.

(Step 4)

This step is the preparation of a compound (I) by reacting a compound (II) with an acid.

In the solvent such as a mixture of acetic acid ester and water such as a mixture of ethyl acetate and water, a mixture of isopropyl acetate and water, a mixture of isobutyl acetate and water, a mixture of n-butyl acetate and water, or a mixture of dichloromethane and water, a compound (I) is obtained from a compound (II) by treating with hydrochloric acid, sulfuric acid, methanesulfonic acid, phosphoric acid, nitric acid to acidify, and the like, and then treating the resulting reaction mixture by usual post-treatment.

To the solution is added a seed crystal if necessary, and a compound (I) is obtained as a crystal from a mixture of acetone and water, a mixture of acetonitrile and water, a mixture of methanol and water, ethyl acetate, a mixture of ethyl acetate and hexane, a mixture of tetrahydrofurane and water, a mixture of N,N-dimethylformamide and water, a mixture of N,N-dimethylacetamide and water, a mixture of dimethylsulfoxide and water, and the like.

A mixture of acetone and water is preferable as a solvent. Preferably the ratio of acetone/water is 2/1 to 1/10. More preferably 1/1 to 1/4.

A preparation of type A crystal of $N^\alpha$-[[2-[5-[[4-methylphenyl]ethynyl]thienyl]]-sulfonyl]-D-tryptophan having substantially a powder X-ray diffraction pattern as shown 19).

A compound (I) is dissolved in methanol or acetone, then the temperature is controlled at 0 to 55° C., preferably 30 to 50° C. To the solution are added water, and a seed crystal if necessary, the solution is stirred for 1 to 5 h, preferably 1 to 2 h, and then the temperature is controlled at 0 to 55° C., preferably 20 to 30° C. and the stirring is continued for 1 to 2 h. The precipitated crystal is filtered and dried to obtain type A crystal.

Type A crystal is obtained by adding a methanol or acetone solution of a compound (I) described above to water containing the seed crystal in a similar manner as above.

A preparation of type B crystal of $N^\alpha$-[[2-[5-[[4-methylphenyl]ethynyl]thienyl]]-sulfonyl]-D-tryptophan having substantially a powder X-ray diffraction pattern as shown 20).

A compound (I) is dissolved in methanol, then the temperature is controlled at 0 to 30° C., preferably 15 to 20° C. To the solution are added water, and a seed crystal if necessary, the solution is stirred at 0 to 30° C., preferably 5 to 20° C. for 0.1 to 2 h, preferably 0.1 to 0.2 h. The obtained monohydrated crystal is filtered, and dried under reduced pressure at 0 to 100° C., preferably 10 to 50° to obtain type B crystal.

A preparation of type C crystal of $N^\alpha$-[[2-[5-[[4-methylphenyl]ethynyl]thienyl]]-sulfonyl]-D-tryptophan having substantially a powder X-ray diffraction pattern as shown 21).

A compound (I) is dissolved in methanol, then the temperature is controlled at 0 to 30° C., preferably 15 to 25° C. To the solution are added water, and a seed crystal if necessary, the solution is stirred at 0 to 30° C. preferably 15 to 20° C. for 0.1 to 2 h, preferably 0.1 to 0.2 h. The obtained monohydrated crystal is filtered, and dried under atmosphere at 0 to 50° C., preferably 10 to 30° to obtain type C crystal.

A compound (I) is dissolved in dimethylsulfoxide. The solution is poured into water at 0 to 60° C. preferably 25 to 45° C., and stirred at 10 to 60° C. preferably 25 to 45 ° C. for 0.1 to 2 h, preferably 0.1 to 0.5 h. The solution is stirred at 0 to 40° C., preferably 10 to 30° C. for 0.1 to 2 h, preferably 0.1 to 0.5 h. The obtained crystal is filtered, and dried under atmosphere at 0 to 50° C., preferably 10 to 30 to obtain type C crystal.

(Conversion of Type B Crystal and/or Type C Crystal to Type A Crystal)

A mixture of methanol and water or a mixture of acetone and water of type B crystal and/or type C crystal is stirred at 0 to 30° C., preferably 20 to 30° C. for 1 to 8 h, preferably 2 to 4 h, or at 30 to 60° C., preferably 40 to 50° C. for 1 to 8 h, prefer h to convert it into type A crystal.

The following examples and examinations provide further illustrate of the present invention. However, they are not to be constructed as limiting the scope thereof.

Abbreviations described below are used in the following examples.

Me: methyl
NMM: N-methylmorpholine

EXAMPLE

Example 1

Preparation of a Compound (III-1)

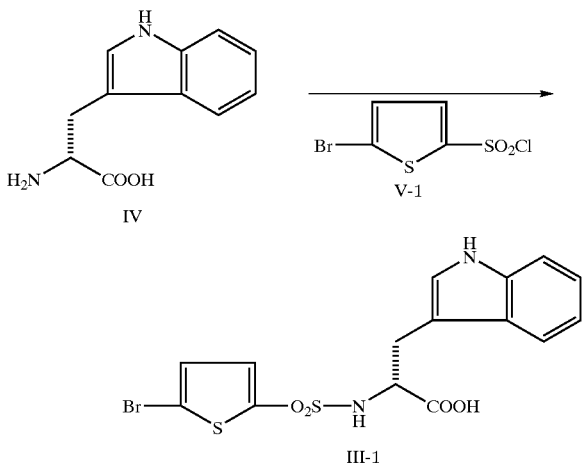

A suspension of sodium carbonate (259 g) and a compound (IV, 200 g, 0.98 mol) in a mixture of water (1000 mL) and acetone (750 mL) was cooled at 4° C. To the reaction mixture was added a compound (V-1, 264 g, 1.0 mol), and then the reaction mixture was stirred at 4° C. for 2 h. The reaction mixture was extracted with water (2900 mL) and ethyl acetate (1410 mL), and then the aqueous layer was washed with ethyl acetate. To the aqueous layer were added ethyl acetate and hydrochloric acid, and the desired compound was extracted to the organic layer. After confirming the organic layer is acidic, the organic layer was washed with brine, and concentrated to obtain a ethyl acetate solution (700 mL) of a compound (III-1, in about 95% yield by calculating from content of a compound (III-1))

$^1$H-NMR (DMSO-$d_6$, ppm) δ 2.90 (dd, J=14.7, 8.7 Hz, 1H, CH), 3.11 (dd, J=14.7, 5.4 Hz, 1H, CH), 3.97 (q-like, J=8.7, 5.4 Hz, 1H, CH), 6.95–7.39 (m, 7H, Ar—H), 8.65 (d, J=8.5 Hz, 1H, SO$_2$NH), 10.83 (s, 1H, ArNH), 12.8 (brs, 1H, CO$_2$H).

Example 2

Preparation of a Compound (II-1)

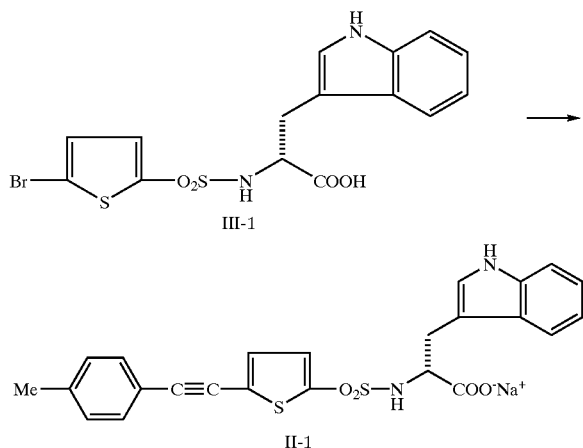

To a concentrated ethyl acetate solution (22.5 mL) containing a compound (III-1, equivalent to 24 mmol of a compound (IV)) were added water (2.5 g), and p-tolylacetylene (2.84 g, 0.024 mol), bistriphenylphosphinepalladium (II) chloride (0.43 g, 0.6 mmol), copper iodide (0.23 g, 1.2 mmol), and triethylamine (4.95 g, 0.048 mol). The reaction mixture was heated at 60° C., and then stirred for about 2 h. The reaction mixture was added to a mixture of brine (41 mL), ethyl acetate (40 mL), and hydrochloric acid (3.8 g). After confirming the reaction mixture is acidic, the organic layer was separated and washed with brine. The extract was filtered through activated carbon, and then methanol (13 mL) and an aqueous sodium hydroxide solution were added to the filtrate. After confirming the resulting mixture is basic, a seed crystal was added to the mixture. The resulting precipitate was filtered and dried to obtain a compound (II-1, 9.4 g, content was 8.6 g). Overall yield of a compound (II-1) from a compound (IV) was 74%.

$^1$H-NMR (DMSO-$d_6$, ppm) δ 2.35(s, 3H, CH$_3$), 3.09 (dd, J=15.0, 8.7 Hz, 1H, CH), 3.16(dd, J=15.0, 4.5 Hz, 1H, CH), 3.50 (q-like, J=8.7, 4.5 Hz, 1H, CH), 6.89–7.58 (m, 11H, Ar—H), 10.69 (s, 1H, ArNH).

Example 3

Preparation of a Compound (II-1)

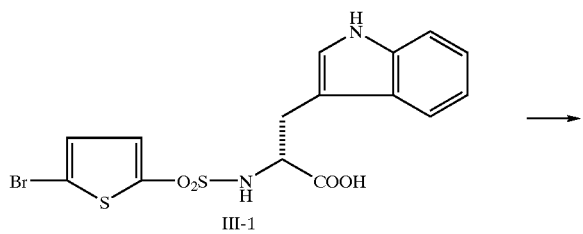

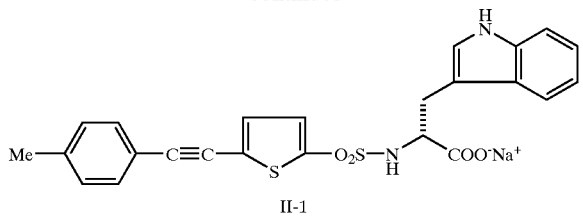

To a concentrated ethyl acetate solution (18.82 g, containing water (0.96%)) containing a compound (III-1, equivalent to 24.5 mmol of a compound (IV)) were added p-tolylacetylene (2.84 g, 0.024 mol), bistriphenylphosphine-palladium (II) chloride (0.17 g, 0.24 mmol), copper bromide (0.07 g, 0.48 mmol), and triethylamine (4.95 g, 0.048 mol), and then the reaction mixture was heated at about 60° C. and stirred for about 3 h. An additional p-tolylacetylene was added to the reaction mixture in midway of reaction. The reaction mixture was added to a mixture of brine (41 mL), ethyl acetate (40 mL), and hydrochloric acid (3.8 g). After confirming the reaction mixture is acidic, the organic layer was separated and washed with brine. The extract was filtered through activated carbon, and then methanol (13 mL) and an aqueous sodium hydroxide solution were added to the filtrate. After confirming the resulting mixture is basic, a seed crystal was added to the mixture. The resulting precipitate was filtered and dried to obtain a compound (II-1, 9.2 g). Overall yield of a compound (II-1) from a compound (IV) was 72.5%.

Example 4

Preparation of a Compound (II-2)

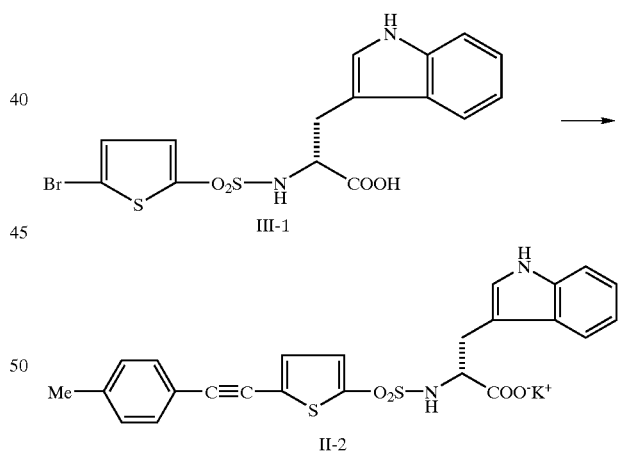

To a concentrated ethyl acetate solution (22.5 mL) containing a compound (III-1, equivalent to 24 mmol of a compound (IV)) were added water (2.5 g), p-tolylacetylene (2.84 g, 0.024 mol), bistriphenylphosphinepalladium (II) chloride (0.43 g, 0.6 mmol), copper iodide (0.23 g, 1.2 mmol), and triethylamine (4.95 g, 0.048 mol). And then the reaction mixture was heated at about 60° C. and stirred for about 2 h. The reaction mixture was added to a mixture of brine (41 mL), ethyl acetate (40 mL), and hydrochloric acid (3.8 g). After confirming the resulting mixture is acidic, the organic layer was separated and washed with brine. The extract was filtered through activated carbon, and then methanol (13 mL) and an aqueous sodium hydroxide solution were added to the filtrate. After confirming the resulting mixture is basic, a seed crystal was added to the extract. The resulting precipitate was filtered and dried to obtain a compound (II-2, 9.9 g, content was 9.0 g). Overall yield of a compound (II-2) from a compound (IV) was 75%.

$^1$H-NMR (DMSO-d$_6$, ppm) δ 2.35 (s, 3H, CH$_3$), 3.11 (q-like, J=5.1, 4.2 Hz, 2H, CH), 3.51 (dd, J=5.1, 4.2 Hz, 1H, CH), 6.89–7.58 (m, 11H, Ar—H), 10.69 (s, 1H, ArNH).

Example 5

Preparation of a Compound (II-3)

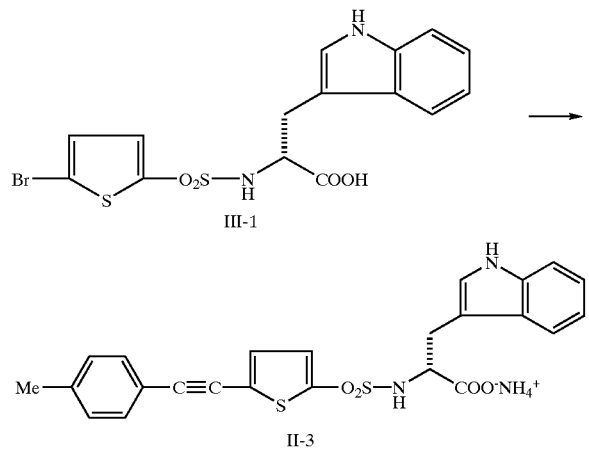

To a concentrated ethyl acetate solution (22.5 mL) containing a compound (III-1, equivalent to 24 mmol of a compound (IV)) were added water (2.5 g), p-tolylacetylene (2.84 g, 0.024 mol), bistriphenylphosphinepalladium (II) chloride (0.43 g, 0.6 mmol), copper iodide (0.23 g, 1.2 mmol), and triethylamine (4.95 g, 0.048 mol), and then the reaction mixture was heated at about 60° C. and stirred for about 2 h. The reaction mixture was added to a mixture of brine (41 mL), ethyl acetate (40 mL), and hydrochloric acid (3.8 g). After confirming the resulting mixture is acidic, the organic layer was separated and washed with brine. The extract was filtered through activated carbon, and then methanol (13 mL) and an aqueous ammonium hydroxide solution were added to the filtrate. After confirming the resulting mixture is basic, a seed crystal was added to the mixture. The resulting precipitate was filtered and dried to obtain a compound (II-3, 9.5 g, content was 8.6 g). Overall yield of a compound (II-3) from a compound (IV) was 75%.

$^1$H-NMR (DMSO-d$_6$, ppm) δ 2.35 (s, 3H, CH$_3$), 3.08 (d, J=5.1 Hz, 2H, CH), 3.50(t, J=5.1 Hz, 1H, CH), 6.92–7.54 (m, t1H, Ar—H), 10.70 (s, 1H, ArNH).

Example 6

Preparation of a Compound (II-1)

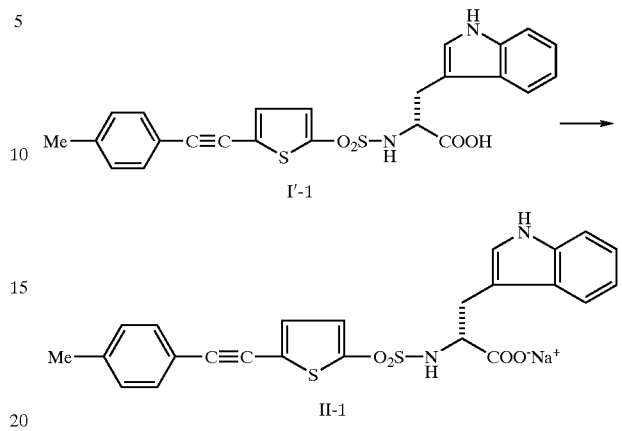

To a Sonogashira reaction mixture containing a compound (I'-1, equivalent to 12.9 mmol of a compound (IV)) were added ethyl acetate (28 mL), water (25 mL), and hydrochloric acid (2 g). After confirming the reaction mixture is acidic, the organic layer was separated and washed with brine. Methanol (13 mL) and 20% sodium hydroxide aqueous solution (5 g) were added to the extract. After confirming the resulting mixture is basic, a seed crystal was added to the mixture, and then the mixture was stirred at room temperature for 3 h. The resulting precipitate was filtered and dried to obtain a compound (II-1, 5.4 g). Overall yield of a compound (II-1) from a compound (IV) was 72%. Its palladium content was 24 ppm.

Example 7

Preparation of a Compound (II-3)

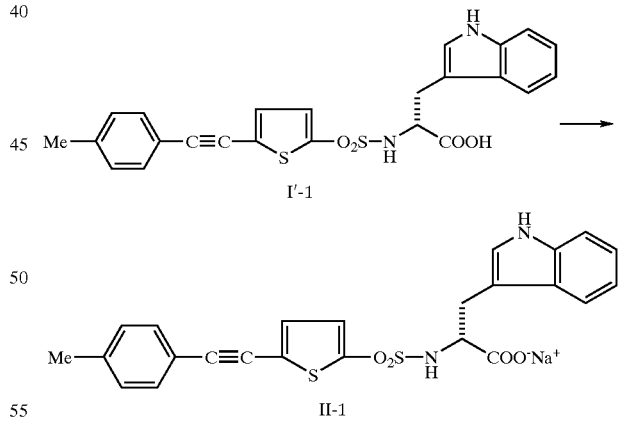

To a Sonogashira reaction mixture containing a compound (I'-1, equivalent to 12.9 mmol of a compound (IV)) were added ethyl acetate (28 mL), water (25 mL), and hydrochloric acid (2 g). After confirming the reaction mixture is acidic, the organic layer was separated and washed with brine. Methanol (7 mL) and 28% methylate (4.8 g) were added to the extract. After confirming the resulting mixture is basic, a seed crystal was added to the mixture, and then the mixture was stirred at room temperature for 3 h. The resulting precipitate was filtered and dried to obtain a compound (II-1, 4.7 g). Overall yield of a compound (II-I) from a compound (IV) was 66%. Its palladium content was 24 ppm.

Example 8

Preparation of a Compound (II-3) by Using Palladium on Carbon

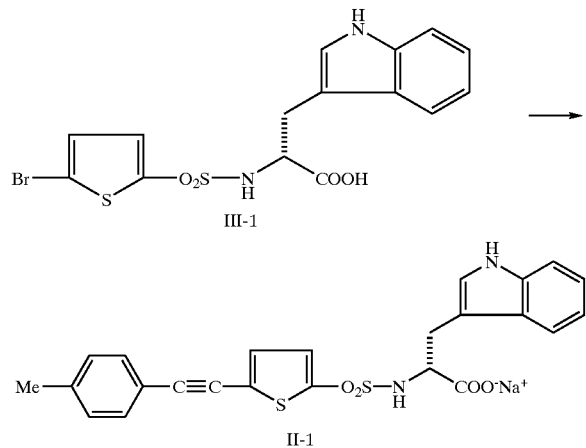

A compound (III-1, 216 mg, purity about 97%), p-tolylacetylene (80 mg, 0.69 mmol), 10% palladium (0) on carbon (15.1 m g, 0.03 eq), copper iodide (5 mg, 0.05 eq), N,N-dimethylformamide (DMF, 1.1 mL), and triethylamine (90 mg, 1.8 eq) were placed into a reactor, and then the reaction mixture was heated at about 60° C. and stirred for about 2 h. The reaction mixture was added to a mixture of brine, ethyl acetate, and hydrochloric acid. After confirming the resulting mixture is acidic, the organic layer was separated and washed with brine. The extract was filtered through activated carbon, and then methanol (13 mL) and an aqueous sodium hydroxide solution were added to the filtrate. After confirming the resulting mixture is basic, a seed crystal was added to the mixture. The resulting precipitate was filtered and dried to obtain a compound (II-1, 180 mg). Overall yield of a compound (II-1) from a compound (IV) was 70%.

Example 9

Preparation of a Compound (I)

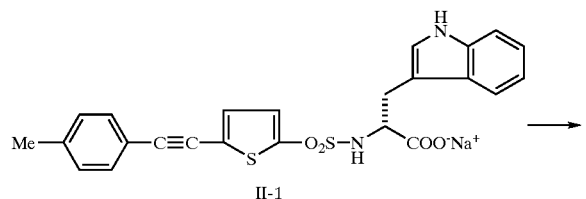

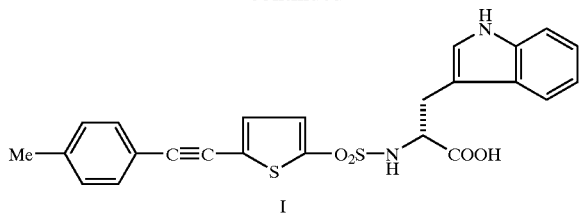

A compound (II-1, 210 g, purity 91%, net content 191 g) was dissolved in ethyl acetate (2430 mL), water (1050 mL), and hydrochloric acid (90 g). After confirming the mixture is acidic, the organic layer was separated. Ethyl acetate of the extract was removed to obtain a compound (I, 182 g, 100%).

Example 10

Preparation of Type A Crystal of a Compound (I)

A methanol solution (380 mL) of a compound (I, 16.1 g) was prepared. After controlling the temperature of the solution at 45° C., to the solution were added water (30 mL), a seed crystal (0.01 g), and more water (120 mL), and then the mixture was stirred for about 1 h. The mixture was cooled to room temperature and then was stirred for about further 1 h. The resulting crystal was filtered and dried to obtain a type A crystal of compound (I, 15.8 g). Yield of this step was 98%.

The powder X-ray diffraction was measured under condition described below. Namely, a Model RAD-II C powder X-ray diffraction measurement apparatus made by RIGAKU DENKI, target Cu, tube voltage 40 kV, tube current 40 mA, graphitemonochrometer, slit DS=0.5°, RS=0.3 mm, ss=1.0°, $RS_m$=0.6 mm, scan speed 3°/min, detector scintilation counter, and revolved sampling stand, measuring range: 5 to 40°, cell of sample: φ5 mm.

A powder X-ray diffraction pattern of the obtained type A crystal has a primary peak at a diffraction angle (2θ)=10.86, 18.14, 19.62, 21.60, 22.74, 23.38, 25.54, 27.22 and 28.12 (degree). The measured diffraction pattern was shown in FIG. 1.

Example 11

Preparation of Type A Crystal of a Compound (I)

A acetone solution (1600 mL) of a compound (I, 170 g) was prepared. After controlling the temperature of the solution at 40° C., to a mixture of water (1970 mL) and a seed ctystal was added dropwise the acetone solution at 40° C. The mixture was cooled to room temperature and the resulting crystal was filtered and dried to obtain a type A crystal of compound (I, 163 g). Yield of this step was 96%. Powder X-ray diffraction pattern of this crystal was identified with the value described at Example 10.

Example 12

Preparation of Type B Crystal of a Compound (I)

After a methanol solution (380 mL) of a compound (I, 16.1 g) was prepared, to the solution were added water (30 mL) and a seed ctystal (0.01 g) at room temperature. To the mixture was added water (120 ml) additionally, and then the mixture was stirred at room temperature for about 20 min. The resulting monohydrated crystal was filtered and dried at about 50 to 80° C. to obtain a type A crystal of compound (I, 15.8 g). Yield of this step was 98%. Powder X-ray diffraction was measured under the same condition used at Example 10.

Figure 2:
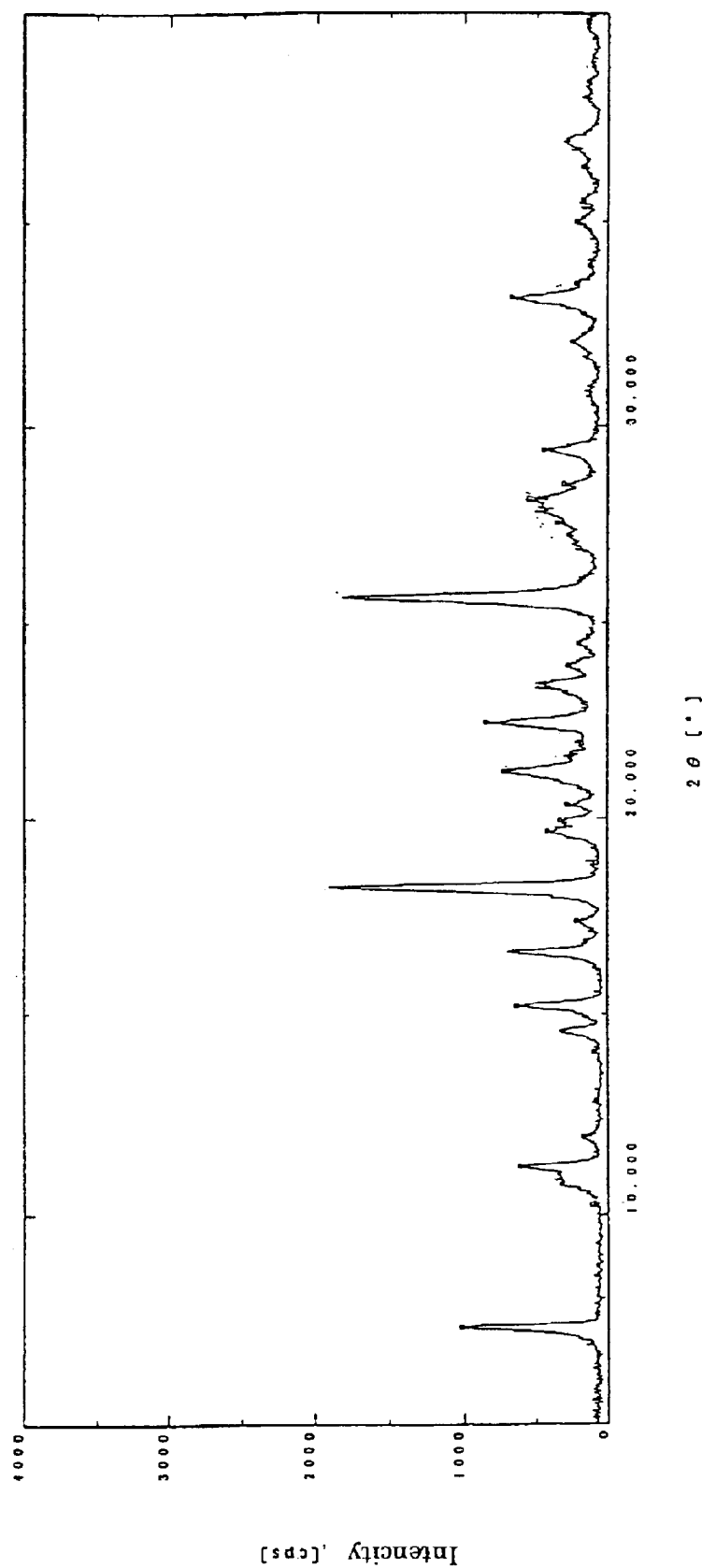
FIG. 2: The chart shows a powder X-ray diffraction of type B crystal obtained in Example 11.

A powder X-ray diffraction pattern of the obtained type B crystal has a primary peak at a diffraction angle (2θ)=7.28, 11.18, 15.20, 16.58, 18.24, 21.20, 22.46, 25.66 and 33.16 (degree). The measured diffraction pattern was shown in FIG. 2.

Example 13

Preparation of Type C Crystal of a Compound (I)

A compound (I, 1 g) was dissolved in dimethylsulfoxide (DMSO, 2 mL), the solution was added dropwise to water (20 mL) at 45° C. for about 2 min. The mixture was stirred at 40 to 45° C. for 30 min, and then cooled to room temperature, and then the stirring was continued for further 1 h. The resulting crystal was filtered and dried to obtain a monohydrated crystal of compound (I, 0.99 g). Yield of this step was 95% by net content. Powder X-ray diffraction was measured under the same condition used at Example 10.

Figure 3:
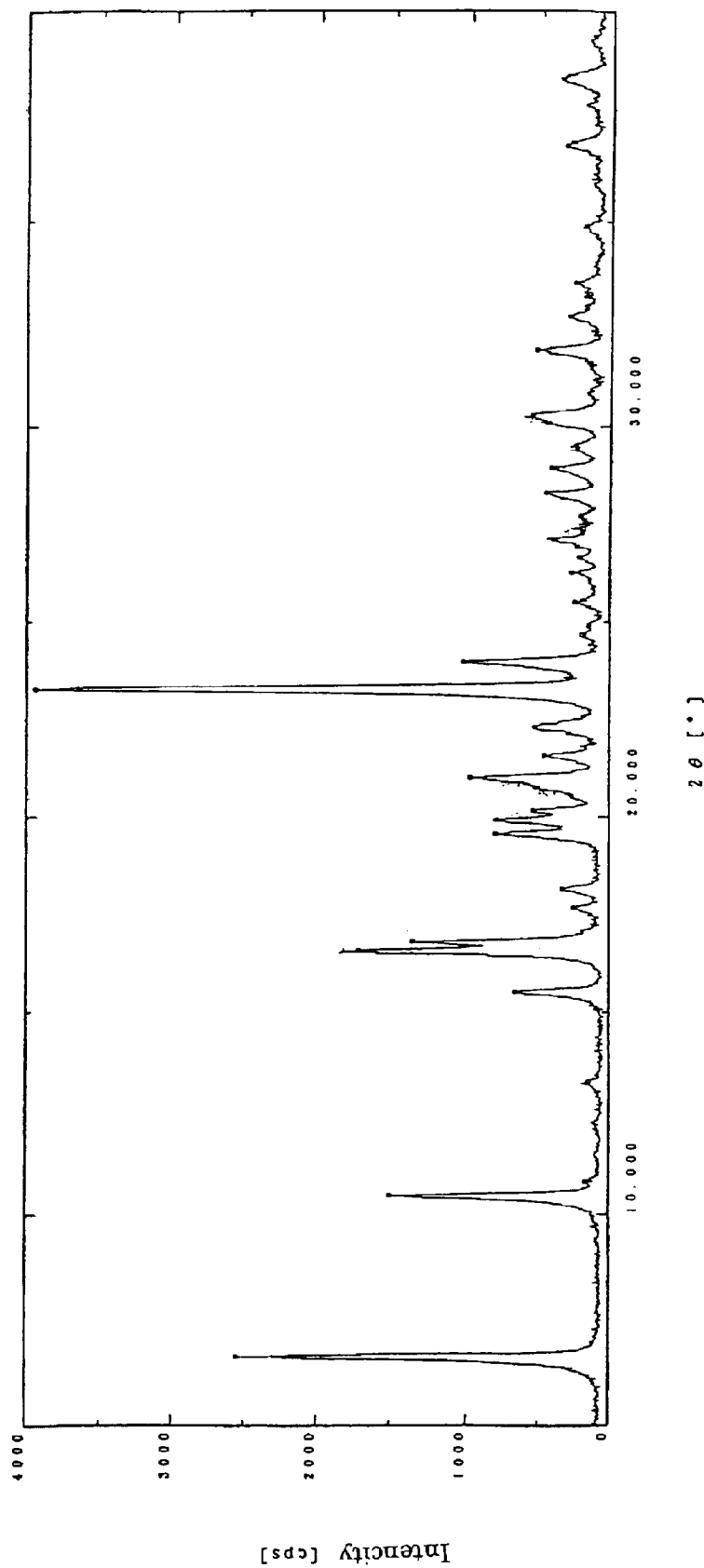
FIG. 3: The chart shows a powder X-ray diffraction of type C crystal obtained in Example 12.

A powder X-ray diffraction pattern of the obtained type C crystal has a primary peak at a diffraction angle (2θ)=6.62, 10.46, 16.58, 16.82, 23.28 and 23.98 (degree). The measured diffraction pattern was shown in FIG. 3.

Example 14

Preparation of Type C Crystal of a Compound (I)

A methanol solution (380 mL) of a compound (I, 16.1 g) was prepared. To the mixture were added water (30 mL) and a seed crystal (0.01 g) at room temperature, and then water (120 mL) was added additionally to the mixture, and then the mixture was stirred at room temperature for about 20 min. The resulting crystal was filtered and dried under atmosphere to obtain a monohydrate crystal of compound (I, 16.4 g). Yield of this step was 98% by net content. Powder X-ray diffraction pattern of this crystal was identified with the value described at Example 13.

Example 15

Preparation of Type A Crystal From Type B Crystal or Type C Crystal of a Compound (I)

A type B crystal or a type C crystal of a compound (I) in methanol solution was stirred at room temperature for 4 h, they were converted into a type A crystal.

Example 16

Preparation of Type A Crystal From Type B Crystal or Type C Crystal of a Compound (I)

A type B crystal or a type C crystal of a compound (I) in methanol solution was stirred at 40° C. for 1 h, they were converted into a type A crystal.

Reference Example 1

Preparation of a Compound (V-1)

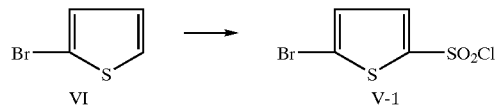

A mixture of chlorosulfonic acid (8 mL, 120 mmol), dichloromethane (30 mL) and phosphorous pentachloride (20.8 g, 100 mmol) was cooled at 0° C. To the mixture, was added a compound (VI, 16.3 g, 100 mmol), and then the mixture was stirred at 0° C. for 2 h. The mixture was heated to 60° C., and then the stirring was continued for 1 h. The mixture was cooled to 35° C., and poured into a mixture of water (30 mL) and chloroform (100 mL). The organic layer was separated and washed with water. The extract was concentrated to 30 g, and hexane (30 mL) was added to the concentrate, then the solution was concentrated again. To the residue were added hexane (25 mL) and a seed crystal, and then the mixture was cooled to crystallize. The resulting precipitate was filtered and dried to obtain a compound (V-1, 23 g), wherein melting point was 40 to 41° C. Yield of this step was 87%. It is possible to use dichloromethane as reaction solvent and extracting solvent.

Reference Example 2

A compound (I) was synthesized according to the schema described below.

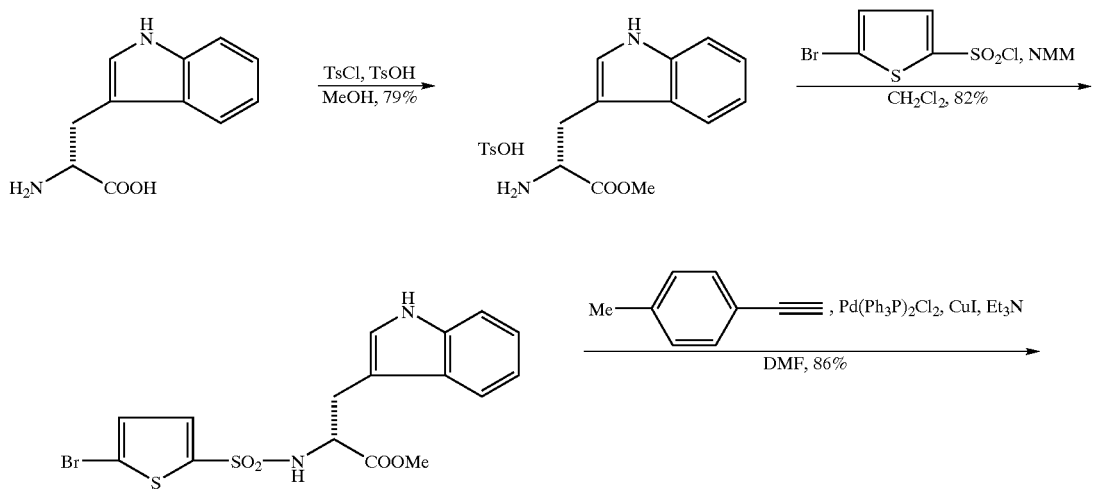

-continued

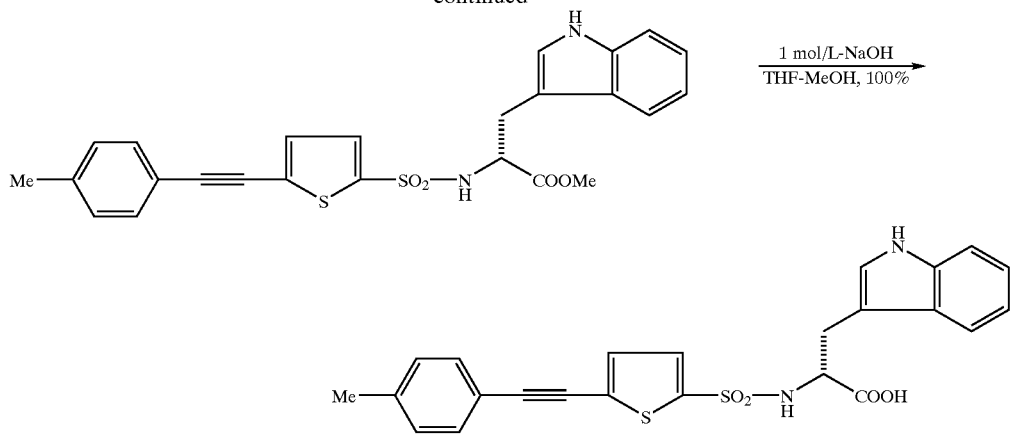

Comparative Example 1

Compared with Example 7 (Without Methanol)

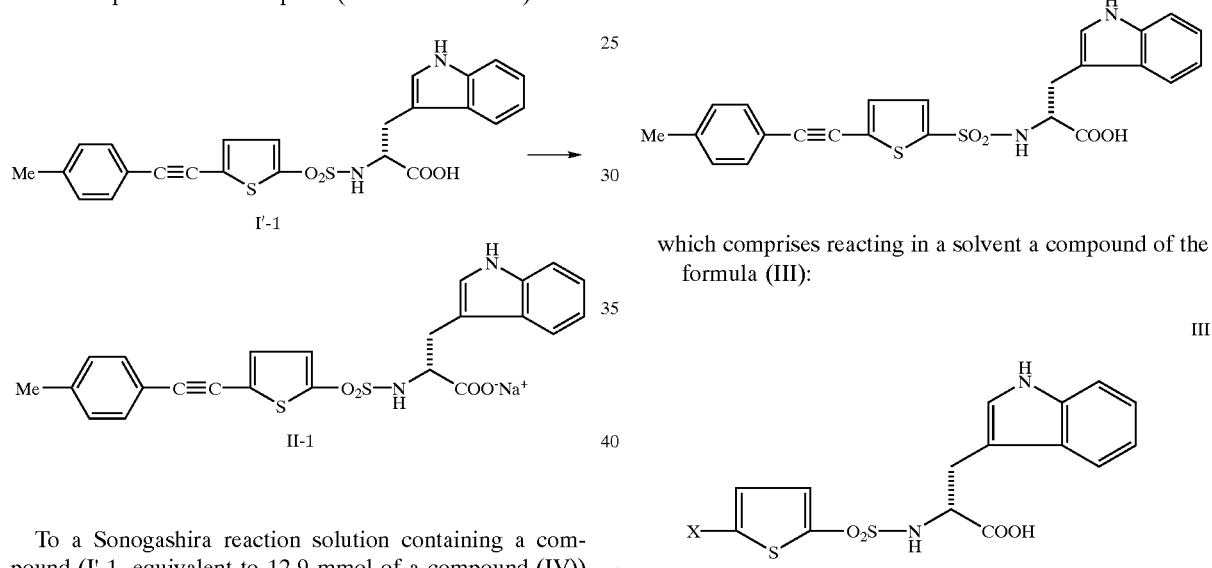

To a Sonogashira reaction solution containing a compound (I'-1, equivalent to 12.9 mmol of a compound (IV)) were added ethyl acetate (28 mL), water (25 mL), and hydrochloric acid (2 g). After confirming the reaction mixture is acidic, the organic layer was separated and washed with brine. To the extract was added 4% sodium hydroxide (25 g). After confirming the mixture is basic, a seed crystal was added to the mixture, and then the mixture was stirred at room temperature for 3 h. The resulting crystal was filtered and dried to obtain a compound (II-1, 4.7 g). Overall yield of a compound (II-1) from a compound (IV) was 66%. Its palladium content was 180 ppm.

INDUSTRIAL APPLICABILITY

In the present invention, a process for the preparation of $N^{\alpha}$-[[2-[5-[[4-methylphenyl]ethynyl]thienyl]]-sulfonyl]-D-tryptophan and crystals thereof are found to be useful as an industrial production and a pharmaceutical formulation.

What is claimed is:

1. A process for the preparation of a compound of the formula (I'):

I' which comprises reacting in a solvent a compound of the formula (III):

III wherein X is halogen, with p-tolylacetylene, a copper (I) salt, a catalyst, and a base, and then treating the resulting reaction mixture with an acid.

2. The process for the preparation of a compound of the formula (II):

II

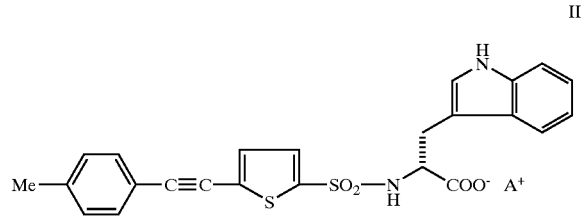

wherein $A^+$ is a cation derived from a basic substance, which comprises reacting in a solvent a compound of the formula (I'):

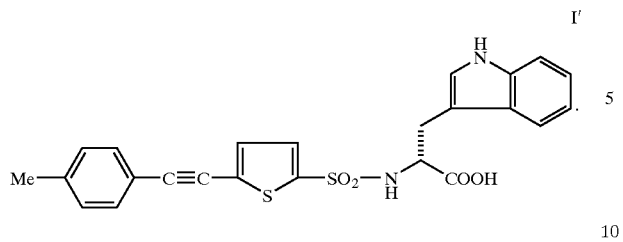

3. The process for the preparation of a compound of the formula (II):

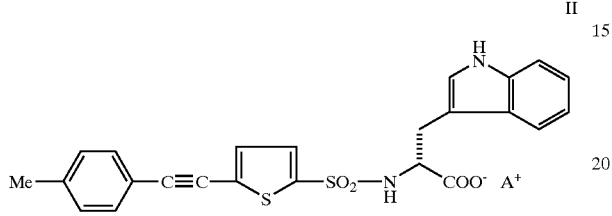

wherein A⁺ is a cation derived from a basic substance, which comprises reacting in a solvent a compound of the formula (I'):

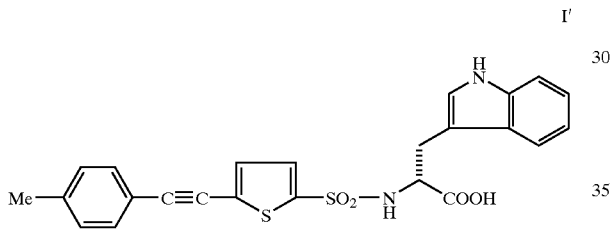

with the basic substance in the presence of an alcohol.
wherein a starting material is the compound (I') obtained by the process according to claim 1.

4. A process for the preparation of a compound of the formula (I)

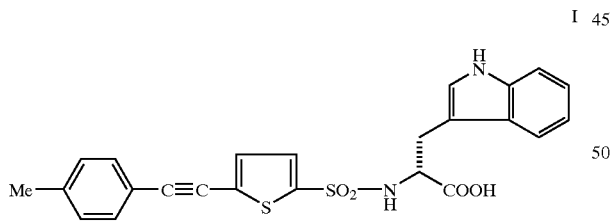

which comprises reacting a compound of the formula (II) obtained by the process according to claim 3:

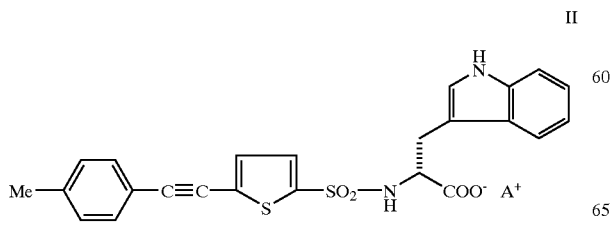

where in A⁺ is a cation derived from a basic substance, with an acid.

5. A process for the preparation of a compound of the formula (III):

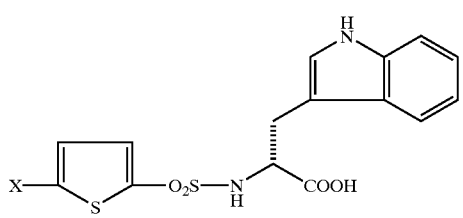

wherein X is halogen;
which comprises reacting in a solvent a compound of the formula (IV):

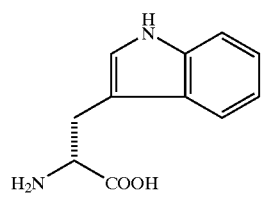

with a compound of the formula (V):

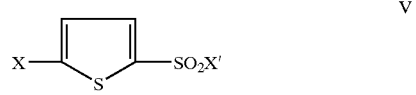

wherein X and X' are independently halogen,
in the presence of a base.

6. A process for the preparation of a compound of the formula (I):

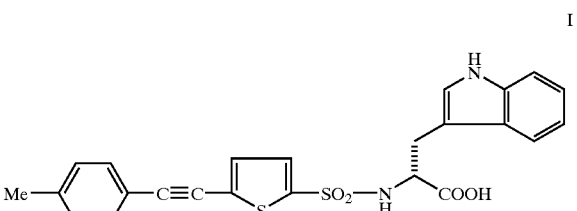

which comprises steps (1) to (4),
(1) a step for the preparation of a compound of the formula (III):

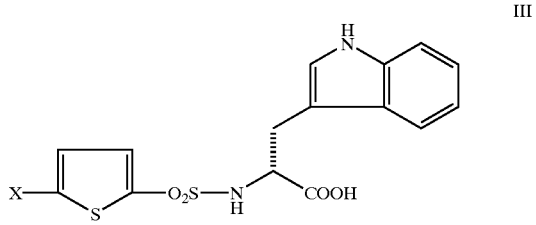

wherein X is halogen,
which comprises reacting in a solvent a compound of the formula (IV):

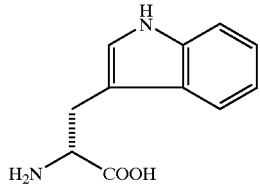

with a compound of the formula (V):

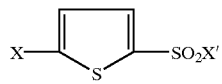

wherein X and X' are independently halogen,
in the presence of a base, (2) a step for the preparation of a compound of the formula (I'):

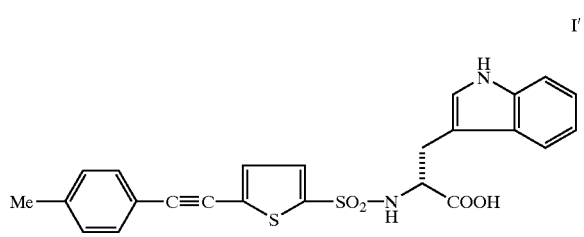

which comprises reacting in a solvent a compound of the formula (III) with p-tolylacetylene, a copper (I) salt, a catalyst, and a base, and then treating the resulting reaction mixture with an acid, (3) a step for the preparation of a compound of the formula (II):

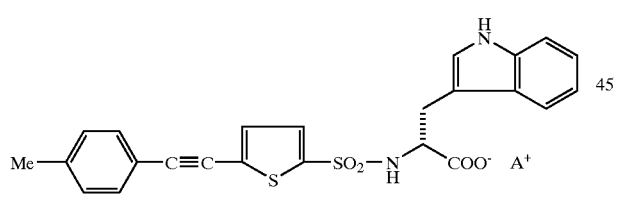

wherein $A^+$ is a cation derived from a basic substance,
which comprises reacting in a solvent a compound of the formula (I'):
with a basic substance, (4) a step for the treatment a compound (II) with an acid.

7. The process according to claim 1 wherein the solvent is N,N-dimethylformamide.

8. The process according to claim 1 wherein the solvent is a mixture of ethyl acetate and water.

9. The process according to claim 1 wherein the catalyst is selected from the group consisting of palladium black, palladium on carbon, bistriphenylphospinepalladium (II) cholride, tetraxis(triphenylphosphine)palladium (0), palladium (II) oxide, palladium (II) chloride, palladium (II) bromide, and palladium (II) acetate.

10. The process according to claim 1 wherein the solvent is N,N-dimethylformamide, and the catalyst is palladium on carbon.

11. The process according to claim 1 wherein the solvent is a mixture of ethyl acetate and water, and the catalyst is bistriphenylphospinepalladium (II) chloride.

12. The process according to claim 1 wherein the solvent is a mixture of ethyl acetate and water, and the catalyst is tetraxis(triphenylphospine)palladium (0).

13. The process according to claim 2 wherein the alcohol is methanol.

14. The process according to claim 2 wherein the basic substance is sodium hydroxide or sodium methoxide.

15. The process according to claim 2 wherein the alcohol is methanol, and the basic substance is sodium hydroxide or sodium methoxide.

16. The process according to claim 5 wherein the solvent is a mixture of acetone and water, and the base is sodium carbonate.

17. A process for the preparation of a compound of the formula (I):

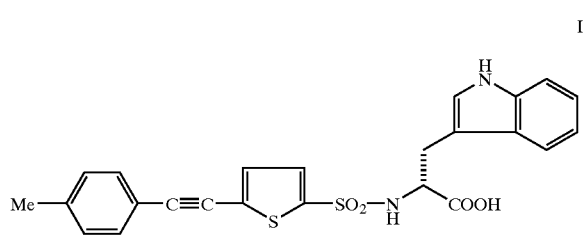

which comprises steps (1) to (2), (1) a step for the preparation of a compound of the formula (II'):

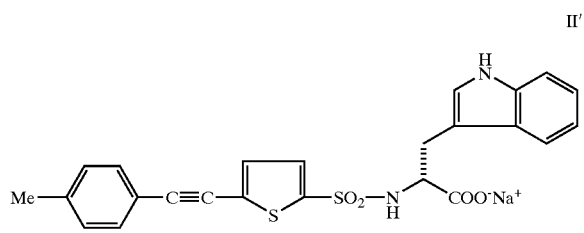

which comprises reacting in a mixture of ethyl acetate and water a compound of the formula (III):

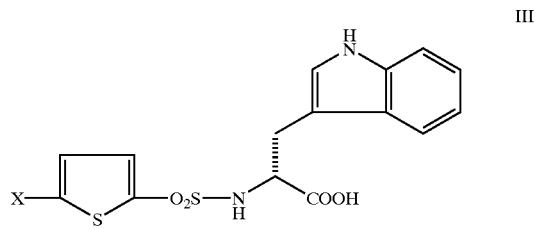

wherein X is halogen,
with p-tolylacetylene, a copper iodide or copper bromide, a bistriphenylphosphinepalladium (II) cholride or tetraxis(triphenylphosphine)palladium (0), and a base, and then treating the resulting reaction mixture with an acid, and then treating the resulting reaction mixture with sodium hydroxide or sodium methoxide in the presence of methanol.

(2) a step for the treatment of the compound (II') with an acid.

* * * * *

UNITED STATES PATENT AND TRADEMARK OFFICE
CERTIFICATE OF CORRECTION

PATENT NO. : 6,831,178 B2
APPLICATION NO. : 10/257752
DATED : December 14, 2004
INVENTOR(S) : Toshiro Konoike et al.

It is certified that error appears in the above-identified patent and that said Letters Patent is hereby corrected as shown below:

Add the following claims 18-21 to the patent: Claims omitted
Col. 27, Line 1

-- 18.   A compound of the formula (II"):

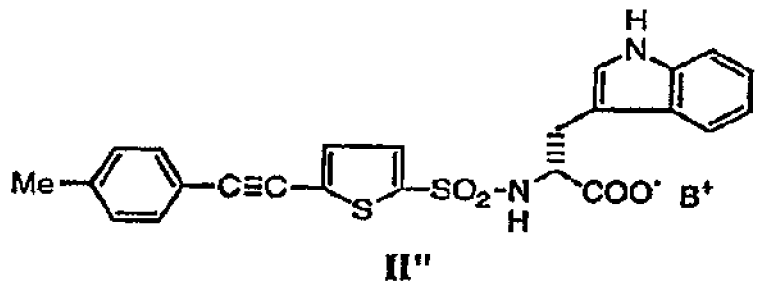

wherein $B^+$ is $Na^+$, $K^+$ or $NH_4^+$.

19.   A crystal of $N^{\alpha}$-[[2-[5-[[4-methylphenyl]ethynyl]thienyl]]sulfonyl]-D-tryptophan wherein a powder X-ray diffraction pattern has a primary peak at a diffraction angle (2θ) = 10.86, 18.14, 19.62, 21.60, 22.74, 23.38, 25.54, 27.22 and 28.12 (degree).

20.   A crystal of $N^{\alpha}$-[[2-[5-[[4-methylphenyl]ethynyl]thienyl]]sulfonyl]-D-tryptophan wherein a powder X-ray diffraction pattern has a primary peak at a diffraction angle (2θ) = 7.28, 11.18, 15.20, 16.58, 18.24, 21.20, 22.46, 25.66 and 33.16 (degree).

UNITED STATES PATENT AND TRADEMARK OFFICE
CERTIFICATE OF CORRECTION

| | |
|---|---|
| PATENT NO. | : 6,831,178 B2 |
| APPLICATION NO. | : 10/257752 |
| DATED | : December 14, 2004 |
| INVENTOR(S) | : Toshiro Konoike et al. |

It is certified that error appears in the above-identified patent and that said Letters Patent is hereby corrected as shown below:

21. A crystal of $N^{\alpha}$-[[2-[5-[[4-methylphenyl]ethynyl]thienyl]]sulfonyl]-D-tryptophan wherein a powder X-ray diffraction pattern has a primary peak at a diffraction angle (2θ) = 6.62, 10.46, 16.58, 16.82, 23.28 and 23.98 (degree). --

Signed and Sealed this

Twenty-seventh Day of February, 2007

JON W. DUDAS
*Director of the United States Patent and Trademark Office*